United States Patent [19]

Markley

[11] 4,254,144
[45] Mar. 3, 1981

[54] SUBSTITUTED BENZONITRILES HAVING ANTIVIRAL ACTIVITY

[75] Inventor: Lowell D. Markley, Midland, Mich.

[73] Assignee: The Dow Chemical Company, Midland, Mich.

[21] Appl. No.: 115,480

[22] Filed: Jan. 25, 1980

[51] Int. Cl.³ .................. A61K 31/275; C07C 121/60; C07C 121/75; C07C 121/78
[52] U.S. Cl. ................. 424/304; 260/465 E; 260/465 F; 260/465 G; 260/465 R
[58] Field of Search .......... 260/465 F, 465 E, 465 G, 260/465 R

[56] References Cited

U.S. PATENT DOCUMENTS

| | | | |
|---|---|---|---|
| 3,711,506 | 1/1973 | Wagner et al. | 260/310 C |
| 3,766,238 | 10/1973 | Rohr et al. | 260/465 F |
| 3,776,961 | 12/1973 | Theisson | 260/613 R |
| 3,813,444 | 5/1974 | Abe et al. | 260/607 A |
| 3,821,312 | 6/1974 | Abe et al. | 260/607 A |
| 4,005,141 | 1/1977 | Moore et al. | 260/556 F |
| 4,039,588 | 8/1977 | Wilson et al. | 260/613 R |
| 4,086,255 | 4/1978 | Moore et al. | 260/556 F |
| 4,106,925 | 8/1978 | Rohr et al. | 71/108 |
| 4,164,412 | 8/1979 | Moore et al. | 71/103 |

FOREIGN PATENT DOCUMENTS 351  1/1979  European Pat. Off. .

Primary Examiner—Dolph H. Torrence

[57] ABSTRACT

Substituted benzonitriles are disclosed having the formula

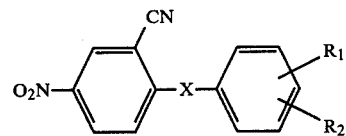

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro. The compounds of the invention exhibit antiviral activity. Methods of use based on the antiviral activity of the compounds are also disclosed, as well as compositions which comprise a carrier in combination with a suitable antiviral active compound.

49 Claims, No Drawings

SUBSTITUTED BENZONITRILES HAVING ANTIVIRAL ACTIVITY

BACKGROUND OF THE INVENTION

Compounds similar in structure to the compounds of the present invention are known in the literature, as for example, those compounds found in U.S. Pat. No. 3,862,209, U.S. Pat. No. 3,798,276 and U.S. Pat. No. 3,231,358. The majority of the literature compounds are utilized for agricultural purposes, primarily as herbicides.

SUMMARY OF THE INVENTION

The present invention is directed to a compound of the formula

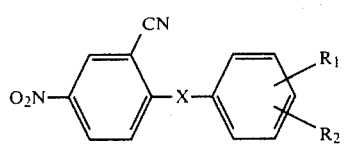

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro. As used in the specification and claims the term "lower alkyl" refers to an alkyl having from one to three carbon atoms such as methyl, ethyl, propyl or isopropyl. Preferred groups include: for $R_1$, bromo, chloro, loweralkylsulfinyl and loweralkylsulfonyl; for $R_2$, hydrogen, bromo, or chloro; and for X, O. For convenience the subject compounds will sometimes be referred to herein as "substituted benzonitriles".

In general, the compounds within the scope of the invention are crystalline compounds having limited water solubility but which are soluble to varying degrees in organic solvents such as methylene chloride, methanol and ethanol. The compounds disclosed herein exhibit antiviral activity and thus can be used to inhibit viral replication by contacting a virus and preferably, virus host cells with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 0.1 microgram ($\mu$g) or less of the active compound per milliliter (ml) of carrier to about 99 percent by weight of the active compound in combination with a pharmaceutically-acceptable carrier.

The compounds of the invention can be prepared by reacting a substituted benzene compound of the formula Bz—A with a substituted benzene compound of the formula Bz′—X—Y, wherein A represents halo, X has the significance set out above with respect to formula I, Y represents hydrogen or a phenate salt forming cation such as sodium or potassium, and wherein Bz represents one of the moieties 2-cyano-4-nitrophenyl or

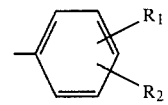

(wherein $R_1$ and $R_2$ have the significance set out with respct to formula I) and Bz′ represents the other of said moieties. The reaction proceeds when the reactants are contacted and mixed, in the presence of phenate salt forming alkali such as an alkali metal hydroxide or carbonate when Y is hydrogen, and in the presence of an inert organic solvent such as dimethyl sulfoxide or acetonitrile. The reaction proceeds well at temperatures of from about 60° C. to about 100° C. and excellent yields are obtained in about 2 to 4 hours, although somewhat more severe conditions can be useful when Bz′ is 2-cyano-4-nitrophenyl. The reactants can be combined in any order and in various proportions, however, the reactants are consumed in equimolar proportions and the use of approximately equimolar proportions is preferred. When Y is hydrogen, an approximately equimolar amount of phenate salt forming alkali is also employed. The compounds can be separated and purified by conventional procedures.

DETAILED DESCRIPTION OF THE INVENTION

The compounds of the present invention are conveniently prepared by reacting a compound of the formula

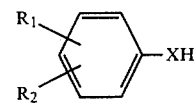

wherein X, $R_1$ and $R_2$ have the same meanings as previously defined herein, with a 2-halo-5-nitrobenzonitrile in an inert organic solvent in the presence of an alkaline agent (also referred to herein as "phenate salt forming alkali") under conditions sufficient to form the subject compound. The alkaline agent should be of sufficient basicity and in sufficient concentration to convert the formula II compound to its appropriate salt for reaction with the 2-halo-5-nitrobenzonitrile.

Alternatively, the compounds can be prepared by reacting a substituted halobenzene of the formula

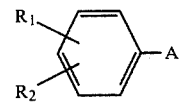

wherein A represents halo, and $R_1$ and $R_2$ have the same meanings as previously defined herein, with a 2-cyano-4-nitrophenol or 1-mercapto-2-cyano-4-nitrobenzene in an inert organic solvent in the presence of an alkaline agent under conditions sufficient to form the subject compound. The alkaline agent in this reaction should be of sufficient basicity and in sufficient concentration to convert the 2-cyano-4-nitrophenol or the 1-mercapto-2-cyano-4-nitrobenzene to its salt for reaction with the compound of formula III. Depending upon the substituents in the formula III compound, more severe reaction conditions can be required than for the reaction of a compound of formula II with a 2-halo-5-nitrobenzonitrile, and/or the reaction can produce more than one of the subject compounds, requiring additional separation steps when a single compound is desired.

In particular, subject compounds have been prepared by at least one of the following methods:

The compound represented by formula II is reacted with a 2-halo-5-nitrobenzonitrile, generally 2-chloro-5-nitrobenzonitrile. The reaction proceeds when approximately equimolar concentrations of the above-noted reactants are contacted and mixed in an inert organic solvent, preferably dimethyl sulfoxide (DMSO) or acetonitrile, and heated at a temperature of from about 60°-100° C. in the presence of an alkaline agent, preferably sodium hydroxide or potassium carbonate, for a time sufficient to obtain the desired subject compound, usually from about 1 hour to about 10 hours is sufficient. Traditional methods, such as dilution with water and filtration, well known in the art can be employed to recover the subject compound from the reaction mixture. Purification is accomplished by conventional techniques such as recrystallization from solvents such as loweralkanols, lower alkyl alkanol ethers, chloroform or dimethylformamide.

Those compounds in which $R_1$ represents loweralkylsulfinyl or loweralkylsulfonyl and X represents O can also be prepared by oxidizing the appropriate parent subject compound of formula I in which $R_1$ represents loweralkylthio and X represents O. The oxidation is conveniently accomplished by oxidizing the sulfur atom of the parent compound with a suitable oxidizing agent as, for example, hydrogen peroxide in glacial acetic acid under conditions in which the desired loweralkylsulfinyl or loweralkylsulfonyl substituent is obtained.

Reactants for the previously described methods of preparing the subject compounds are available commercially or readily prepared by procedures well known in the art. The compound 2-chloro-5-nitrobenzonitrile is commercially available as are most of the substituted phenols and substituted thiophenols represented by formula II. The substituted phenols having a diloweralkylaminosulfonyl substituent are readily prepared utilizing procedures similar to those described in Eliel, et al, *J. Org. Chem.*, 20, 1657 (1955).

As used herein the term "inert organic solvent" refers to organic solvents which do not undergo reaction themselves under the conditions employed for making the subject compounds. Examples of suitable inert organic solvents are dimethyl sulfoxide, acetonitrile, toluene or dimethylformamide. "Alkaline agent" refers to bases capable of forming salts with phenols, such as sodium hydroxide, potassium hydroxide, sodium carbonate and potassium carbonate and "halo" refers to bromo, chloro, fluoro or iodo.

The following examples are included to further illustrate the invention but are not to be construed as a limitation thereon.

EXAMPLE 1—2-(3,4-Dichlorophenoxy)-5-nitrobenzonitrile

To a solution of 91.3 grams (g) (0.56 moles) of 3,4-dichlorophenol dissolved in 500 milliliters (ml) of dimethyl sulfoxide (DMSO) was added 22.4 g (0.56 moles) of sodium hydroxide. The slurry was heated at 60° C. for 15 minutes and 100 g (0.55 moles) of 2-chloro-5-nitrobenzonitrile was added. The mixture was heated at 75° C. for 3 hours (hrs). The reaction mixture was cooled and poured into a slurry of 200 ml of 2 Normal (2 N) sodium hydroxide and 1800 ml of ice and water with the product precipitating. The product was collected by filtration, washed well with water and dried, to obtain 163.3 g of product (96.4% yield), mp 154°-155° C. Recrystallization from 3-methoxy-2-propanol (Dowanol® PM The Dow Chemical Company, Midland, Mich.) afforded purified 2-(3,4-dichlorophenoxy)-5-nitrobenzonitrile, melting at a melting point (mp) of 155°-156° C. The prominent infrared bands for 2-(3,4-dichlorophenoxy)-5-nitrobenzonitrile were as follows: IR (Nujol) 2250, 1620, 1580, 1520, 1465, 1360, 1270, 1130, 1040 and 895 cm$^{-1}$.

EXAMPLE 2—2-(2,4-Dichlorophenoxy)-5-nitrobenzonitrile

To a solution of 5.0 g (0.0307 moles) of 2,4-dichlorophenol dissolved in 150 ml of DMSO was added 1.23 g (0.0307 moles) of sodium hydroxide. The slurry was heated at 60° C. for 15 minutes and 5.04 g (0.0276 moles) of 2-chloro-5-nitrobenzonitrile was added. The mixture was heated at 75° C. for 3.25 hrs. The reaction mixture was cooled and poured into water. The product was collected by filtration, washed well with water and dried, yielding 8.1 g of product (95.3% yield). Recrystallization from ethanol afforded purified 2-(2,4-dichlorophenoxy)-5-nitrobenzonitrile, mp 153.5°-154.5° C.

EXAMPLE 3—2-(4-Bromophenoxy)-5-nitrobenzonitrile

To a solution of 5.31 g (0.0307 moles) of 4-bromophenol dissolved in 150 ml of DMSO was added 1.23 g (0.0307 moles) of sodium hydroxide. The slurry was heated at 60° C. for 15 minutes and 5.04 g (0.0276 moles) of 2-chloro-5-nitrobenzonitrile was added. The mixture was heated at 75° C. for 4 hrs. The reaction mixture was cooled and poured into water. The product was collected by filtration, washed well with water and dried, which gave 8.1 g of crude product. The crude product was dissolved in CH$_2$Cl$_2$ and washed with 10% aqueous sodium hydroxide, water and dried (Na$_2$SO$_4$). Removal of solvent in vacuo gave 7.5 g (85% yield) of product. Recrystallization from ethanol afforded purified 2-(4-bromophenoxy)-5-nitrobenzonitrile, mp 171°-172° C.

EXAMPLE 4—2-(4-Chlorophenoxy)-5-notrobenzonitrile

To a solution of 3.95 g (0.0307 moles) of 4-chlorophenol dissolved in 150 ml of DMSO was added 1.23 g (0.0307 moles) of sodium hydroxide. The slurry was heated at 60° C. for 15 minutes and 5.04 g (0.0276 moles) of 2-chloro-5-nitrobenzonitrile was added and the mixture was heated at 75° C. for 3 hrs. The reaction mixture was cooled and poured into water. The product was collected by filtration, washed well with water and dried, to produce 7.0 g of the product (92% yield). Recrystallization from ethanol afforded purified 2-(4-chlorophenoxy)-5-nitrobenzonitrile, mp 163°-164° C.

EXAMPLE 5—2-(4-Phenoxyphenoxy)-5-nitrobenzonitrile

To a solution of 5.71 g (0.0307 moles) of 4-phenoxyphenol dissolved in 150 ml of DMSO was added 1.23 g (0.0307 moles) of sodium hydroxide. The slurry was heated at 75° C. for 15 minutes and 5.04 g (0.0276 moles) of 2-chloro-5-nitrobenzonitrile was added and the mixture heated at 75° C. for 4 hrs. The reaction mixture was cooled and poured into water. The product was collected by filtration, washed well with water and dried. The crude product was dissolved in $CH_2Cl_2$ and washed with 10% aqueous sodium hydroxide, water and dried ($Na_2SO_4$). Removal of solvent in vacuo afforded 8.0 g (87% yield) of product. Recrystallization from ethanol gave purified 2-(4-phenoxyphenoxy)-5-nitrobenzonitrile, mp 150°–151.5° C.

EXAMPLE 6—2-(4-(Methylthio)phenoxy)-5-nitrobenzonitrile

To a solution of 11.55 g (0.0824 moles) of 4-(methylthio)phenol dissolved in 150 ml of DMSO was added 3.3 g (0.0824 moles) of sodium hydroxide. The slurry was heated to 60° C. and 13.7 g (0.0730 moles) of 2-chloro-5-nitrobenzonitrile was added and the mixture heated at 75° C. for 2½ hrs. The mixture was cooled and poured into a solution of 200 ml of 5 N aqueous sodium hydroxide and 500 ml of water. The product was collected by filtration, washed well with water and dried, to obtain 20.3 g of product (94.6% yield). Recrystallization from methanol afforded purified 2-(4-(methylthio)phenoxy)-5-nitrobenzonitrile, mp 124°–126° C.

EXAMPLE 7—2-(4-Methylsulfinyl)phenoxy)-5-nitrobenzonitrile

To a slurry of 10.0 g (0.0350 moles) of 2-(4-(methylthio)phenoxy)-5-nitrobenzonitrile in 100 ml of glacial acetic acid was added a solution of 4.0 g of aqueous 30 percent (30%) hydrogen peroxide (0.0350 moles) dissolved in 20 ml of glacial acetic acid over 5 minutes. The reaction mixture was stirred at room temperature for 16 hrs and heated at 50° C. for 3 hrs. The reaction mixture was poured into water and the product collected by filtration, washed well with water and dried to obtain 9.8 g of product (92.8% yield). Recrystallization from ethanol afforded purified 2-(4-(methylsulfinyl)phenoxy)-5-nitrobenzonitrile, mp 159°–160° C.

EXAMPLE 8—2-(4-(Methylsulfonyl)phenoxy)-5-nitrobenzonitrile

To a slurry of 10.0 g (0.0350 moles) of 2-(4-(methylthio)phenoxy)-5-nitrobenzonitrile in 75 ml of glacial acetic acid heated at 60° C. was added 15.85 g of aqueous 30% hydrogen peroxide (0.140 moles) over 5 minutes. An additional 25 ml of glacial acetic acid was added and the mixture heated at 75° C. for 3 hrs. The reaction mixture was cooled and poured into water. The product was collected by filtration, washed with water and dried to obtain 10.9 g of product (98.2% yield), mp 205°–206.5° C. Recrystallization from methanol gave purified 2-(4-methylsulfonyl)phenoxy)-5-nitrobenzonitrile, mp 206°–207° C.

EXAMPLE 9—N,N-Dimethyl-4-(2-cyano-4-nitrophenoxy)benzenesulfonamide

To a solution of 6.37 g (0.0317 moles) of N,N-dimethyl-4-hydroxybenzenesulfonamide in 150 ml of DMSO was added 1.27 g (0.0317 moles) of sodium hydroxide. The mixture was heated to 60° C. and 5.26 g (0.0288 moles) of 2-chloro-5-nitrobenzonitrile added and the mixture heated at 75° C. for 2½ hrs. The reaction mixture was cooled and poured into a solution of 400 ml of 2 N aqueous sodium hydroxide and 300 ml of water. The product was collected by filtration, washed well with water and dried to obtain 8.8 g of product (88% yield). Recrystallization from a mixture of ethanol and dimethylformamide afforded purified N,N-dimethyl-4-(2-cyano-4-nitrophenoxy)benzenesulfonamide, mp 221.5°–223° C.

EXAMPLE 10—N,N-Diethyl-4-(2-cyano-4-nitrophenoxy)benzenesulfonamide

To a solution of 6.73 g (0.0294 moles) of N,N-diethyl-4-hydroxybenzenesulfonamide in 150 ml of DMSO was added 1.18 g (0.0294 moles) of sodium hydroxide. The mixture was heated to 60° C. and 4.88 g (0.0267 moles) of 2-chloro-5-nitrobenzonitrile was added and the mixture heated at 75° C. for 3 hrs. The reaction mixture was cooled and poured into a solution of 400 ml of 2 N aqueous sodium hydroxide and 300 ml of water. The product was collected by filtration, washed well with water and dried to obtain 8.8 g of product (88% yield). Recrystallization from ethanol afforded purified N,N-diethyl-4-(2-cyano-4-nitrophenoxy)benzenesulfonamide, mp 163°–164° C.

EXAMPLE 11—2-(4-Benzoylphenoxy)-5-nitrobenzonitrile

To a solution of 11.4 g (0.0575 moles) of 4-hydroxybenzophenone dissolved in 150 ml of DMSO was added 2.3 g (0.0575 moles) of sodium hydroxide. The mixture was heated to 60° C. and 10.0 g (0.0548 moles) of 2-chloro-5-nitrobenzonitrile was added and the mixture heated at 75° C. for 3 hrs. The reaction mixture was cooled and poured into a solution of 100 ml of 2 N aqueous sodium hydroxide and 700 ml of water. The product was collected by filtration, washed well with water and dried to obtain 17.75 g of product (89.6% yield). Recrystallization from a mixture of ethanol and dimethylformamide and a second recrystallization from chloroform afforded purified 2-(4-benzoylphenoxy)-5-nitrobenzonitrile, mp 179.5°–180.5° C.

EXAMPLE 12—2-((4-Chlorophenyl)thio)-5-nitrobenzonitrile

To a solution of 15.2 g (0.105 moles) of 4-chlorothiophenol dissolved in 150 ml of DMSO was added 4.2 g (0.105 moles) of sodium hydroxide. The mixture was heated to 60° C. and 18.3 g (0.100 moles) of 2-chloro-5-nitrobenzonitrile was added and the mixture heated at 60° C. for 2½ hrs. The mixture was cooled and poured into a solution of 100 ml of 2 N aqueous sodium hydroxide and 600 ml of water. The product was collected by filtration, washed well with water and dried to obtain 28.8 g of product (99% yield). Recrystallization from ethanol afforded purified 2-((4-chlorophenyl)thio)-5-nitrobenzonitrile, mp 162°–164.5° C.

The physical properties of the above examples are summarized in Table 1.

TABLE 1

| Compound Example Number | X | $R_1$ | $R_2$ | Mp °C. | Mol. Formula | Mol. Weight | Calculated | | | Found | | |
|---|---|---|---|---|---|---|---|---|---|---|---|---|
| | | | | | | | % C | % H | % N | % C | % H | % N |
| 1 | O | 4-Cl | 3-Cl | 155–156 | $C_{13}H_6Cl_2N_2O_3$ | 309.108 | 50.51 | 1.96 | 9.06 | 50.3 | 1.99 | 9.17 |
| 2 | O | 4-Cl | 2-Cl | 153.5–154.5 | $C_{13}H_6Cl_2N_2O_3$ | 309.108 | 50.51 | 1.96 | 9.06 | 50.7 | 1.97 | 9.20 |
| 3 | O | 4-Br | H | 171–172 | $C_{13}H_7BrN_2O_3$ | 319.118 | 48.93 | 2.21 | 8.78 | 48.9 | 2.21 | 9.05 |

TABLE 1-continued

| Compound Example Number | X | R₁ | R₂ | Mp °C. | Mol. Formula | Mol. Weight | Calculated % C | % H | % N | Found % C | % H | % N |
|---|---|---|---|---|---|---|---|---|---|---|---|---|
| 4 | O | 4-Cl | H | 163–164 | $C_{13}H_7ClN_2O_3$ | 274.659 | 56.85 | 2.57 | 10.20 | 56.6 | 2.52 | 10.29 |
| 5 | O | 4-O—⟨phenyl⟩ | H | 150–151.5 | $C_{19}H_{12}N_2O_4$ | 332.302 | 68.67 | 3.64 | 8.43 | 68.7 | 3.60 | 8.44 |
| 6 | O | 4-SCH₃ | H | 124–126 | $C_{14}H_{10}N_2O_3S$ | 286.302 | 58.73 | 3.52 | 9.79 | 58.5 | 3.61 | 9.77 |
| 7 | O | 4-SCH₃ (→O) | H | 159–160 | $C_{14}H_{10}N_2O_4S$ | 302.302 | 55.62 | 3.33 | 9.27 | 55.5 | 3.38 | 9.47 |
| 8 | O | 4-SO₂CH₃ | H | 206–207 | $C_{14}H_{10}N_2O_5S$ | 318.302 | 52.82 | 3.17 | 8.80 | 52.9 | 3.23 | 8.83 |
| 9 | O | 4-SO₂N(CH₃)₂ | H | 221.5–223 | $C_{15}H_{13}N_3O_5S$ | 347.344 | 51.87 | 3.77 | 12.10 | 51.6 | 3.82 | 12.12 |
| 10 | O | 4-SO₂N(C₂H₅)₂ | H | 163–164 | $C_{17}H_{17}N_3O_5S$ | 375.396 | 54.39 | 4.56 | 11.19 | 54.6 | 4.55 | 11.23 |
| 11 | O | 4-C(=O)—⟨phenyl⟩ | H | 179.5–180.5 | $C_{20}H_{12}N_2O_4$ | 344.312 | 69.76 | 3.51 | 8.14 | 69.7 | 3.55 | 8.06 |
| 12 | S | 4-Cl | H | 162–164.5 | $C_{13}H_7ClN_2O_2S$ | 290.725 | 53.70 | 2.43 | 9.64 | 53.5 | 2.52 | 9.56 |

The compounds of the invention have antiviral activity, and have been found to be particularly effective against picornaviruses, i.e., the small ribonucleic acid viruses. The picornaviruses include viruses such as Coxsackieviruses, Rhinoviruses and a number of plant disease viruses. The compounds have low mammalian toxicity, low phototoxicity and exhibit little or no detrimental side effects when administered to mammals at dosages consistent with good antiviral activity. There is some compound-to-comound variation in antiviral potency and spectrum of antiviral activity, and in toxicity and side effects, as illustrated below.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture mediums such as those described herein are more fully described in standard texts, as for examle, Kuchler's Biochemical Methods in Cell Culture and Virology, Dowden, Hutchinson and Ross, Inc., Stroudsberg, Pa. (1977). Following treatment, cells were challenged with 0.05 ml of rhinovirus type 1A (RV-1A), rhinovirus type 2 (RV-2) or Coxsackie $A_{21}$ virus (Cox $A_{21}$) in culture medium. Some of the compounds were also tested against rhinovirus type 5 (RV-5), rhinovirus type 8 (RV-8) or rhinovirus type 64 (RV-64). Cell controls received no viruses. Cultures were observed for compound cytotoxicity and viral cytopathic effect (CPE) at 48 and 72 hours post-treatment.

In addition, some of the compounds were tested in animals utilizing the following procedure, hereinafter referred to as the "Single Oral Dose" test. Swiss male mice, 10–12 grams in weight were challenged intraperitoneally (IP) with 0.2 ml of a normally lethal dose, i.e. a virus dose sufficient to cause $\cong$80–100% mortality in infected animals within 10 days of challenge of Cox $A_{21}$, in phosphate buffered saline containing 1% heat inactivated fetal calf serum. Three hours later mice were treated orally (P.O.) with 0.2 ml of compound suspended in 0.5% hydroxypropyl methylcellulose (Methocel) or with 0.2 ml of 0.5% Methocel containing no compound. Compound suspensions had a concentration of 30 milligrams (mg)/ml (600 mg/kg). Mice were observed daily for 7–10 days post-challenge and deaths recorded. A modified Mantel-Haenzel combined chi-square procedure was used to determine significant difference between virus control and treated groups. Chi-square values greater than 3.84 are considered significant (95% confidence level) in this test.

Some of the compounds were also tested in animals utilizing the following procedure, hereinafter referred to as the "Continuous Oral Feeding" test. Coxsackie $A_{21}$ virus grown on HeLa cells was administered at a concentration that produces 80 to 100% deaths in mice weighing 10 to 11 grams within 10 days, when the mice are injected (IP) with 0.2 ml of virus preparation. Mice were placed on diets containing test compound dispersed in plain commercially available rodent mash chow at a concentration of 0.06% (weight percent) on day 0. On day 1 the mice were challenged with the virus preparation, 0.2 ml/mouse, IP. Deaths in both control and experimental groups were recorded for the 10 days and the results analyzed by a chi-square test. Chi-square values greater than 3.84 indicate the compound is active (95% confidence level).

Results obtained from the above-noted testing are summarized in Table 2.

TABLE 2

| Compound Example Number | Cytotoxicity* (μg/ml) | Tissue Culture Testing** | | | | | | Animal Testing | | | |
|---|---|---|---|---|---|---|---|---|---|---|---|
| | | | | | | | | Single Oral Dose | | Continuous Oral Feeding | |
| | | RV-1A | RV-2 | Cox $A_{21}$ | RV-5 | RV-8 | RV-64 | Dose (mg/kg) | $X^2$ | Dose*** | $X^2$ |
| 1 | >100 | 0.5 | 0.25 | 0.25 | 0.5 | 0.25 | 0.156 | 600 | 5.36 | 0.06% | 23.62 |
| 2 | >100 | 0.625 | 0.625 | 1.25 | 2.5 | 2.5 | | 600 | 3.659 | 0.06% | 1.38 |
| 3 | >100 | 1.25 | 1.25 | 2.5 | | | | 600 | 2.139 | 0.06% | 5.81 |
| 4 | >100 | ≦0.625 | ≦0.625 | 0.625 | <0.3 | <6 | | 600 | 0.252 | 0.06% | 10.61 |
| 5 | >100 | NA | 50 | <6.25 | | | | 600 | 0.719 | 0.06% | 0.26 |
| 6 | 100 | NA | ≦6.25 | <6.25 | | | | 600 | 0.609 | 0.06% | 6.91 |
| 7 | 50 | NA | 6.25 | <6.25 | | | | 600 | 18.94 | 0.06% | 18.82 |
| 8 | >100 | NA | 12.5 | <6.25 | | | | 600 | 0.095 | 0.06% | 10.45 |
| 9 | >100 | NA | NA | <6.25 | | | | | | 0.06% | 9.03 |

TABLE 2-continued

| Compound | | | | | | | | Animal Testing | | | |
|---|---|---|---|---|---|---|---|---|---|---|---|
| | | Tissue Culture Testing** | | | | | | Single Oral Dose | | Continuous Oral Feeding | |
| Example Number | Cytotoxicity* ($\mu$g/ml) | RV-1A | RV-2 | Cox $A_{21}$ | RV-5 | RV-8 | RV-64 | Dose (mg/kg) | $X^2$ | Dose*** | $X^2$ |
| 10 | >100 | ±50 | NA | <6.25 | | | | | | 0.06% | 2.84 |
| 11 | >100 | NA | ±100 | 12.5 | | | | 600 | 0.64 | | |
| 12 | 25 | ±3.125 | ≦1.6 | 1.6 | | | | 600 | 4.805 | 0.06% | 0.215 |

*Cytotoxicity figures represent the concentration of the compound, micrograms/milliliter ($\mu$g/ml) found to be toxic to the cell.
**Lowest concentration of the compound ($\mu$g/ml) necessary to cause a 50 percent reduction in cytopathic effect.
***Percent (by weight) of test compound in the diet fed to test animals.
The symbol "NA" indicates that the compound was not active against that particular virus at the standard test conditions; "<" means "less than"; ">" means "greater than"; "≦" means "less than or equal to " and "±" means "approximately".

The data in Table 2 demonstrates the antiviral activity of representative compounds falling within the scope of the present invention.

The tissue culture test data indicates that all of the test compounds are active against at least one of the three test viruses, (RV-1A, RV-2 or Cox $A_{21}$). In addition, several of the test compounds have exhibited antiviral activity with respect to test viruses RV-5, RV-8 or RV-64.

Furthermore, some of the compounds have demonstrated (at the 95% confidence level, i.e., have a $\chi^2$ value greater than 3.84) that they are active antiviral compounds in testing with mice.

Of particular interest is the compound of Example Number 1, i.e. 2-(3,4-dichlorophenoxy)-5-nitrobenzonitrile, which has exhibited antiviral activity in both the "Single Oral Dose" and "Continuous Oral Feeding" tests. A compound which can be administered orally and still retain antiviral activity has distinct advantages since it can be readily incorporated in the diets of mammals, as exemplified in the "Continuous Oral Feeding" test, or orally in various compositions comprising the active compound and a pharmaceutically-acceptable carrier. The compound 2-(3,4-dichlorophenoxy)-5-nitrobenzonitrile has exhibited antiviral activity against a broad spectrum of viruses in other tissue culture testing as follows:

Solutions of 2-(3,4-dichlorophenoxy)-5-nitrobenzonitrile were prepared by dissolving 5 milligrams of the compound in 0.1 ml dimethyl sulfoxide and incubating at 56° C. for at least 15 minutes. This solution was added to 0.9 ml of warmed (56° C.) maintenance medium (49% Eagles, 49% medium 199, 2% fetal calf serum and antibiotics), and the resulting 1.0 ml was then added to 9 ml of warmed (56° C.) maintenance medium. From this solution the final concentrations of 100, 50, 25, or 12.5 $\mu$g/ml were made up with maintenance medium.

Triplicate cell culture tubes (WI-38 human embryonic lung cell culture tubes) were fed with 1 ml of medium containing the compound at specified concentrations and inoculated with 3–300 $TCID_{50}$ (3–300 times the tissue culture infective dose 50, i.e., the dose required to infect 50% of the cell cultures tested. Simultaneous viral titrations were performed. The tissue cultures were supplemented with fresh medium when necessary (around 3-4 days) until viral titrations were completed.

The cell culture tubes were examined daily for cytopathic effect. Tests were judged complete when virus control titration tubes showed 75% or greater destruction of cell sheets. Comparisons were made at that time with the percentage of cell sheet destruction in tubes containing virus compound mixtures. Observed differences of 75% or more were graded "+," 74–50% at "±," and less than 50% as "—" inhibition.

In the above-noted tests, the compound 2-(3,4-dichlorophenoxy)-5-nitrobenzonitrile at a concentration of 25 micrograms per milliliter ($\mu$g/ml) inhibited the multiplication of 20 different rhinoviruses, i.e., was graded as "+" against the 20 different rhinoviruses utilized for testing, which viruses were as follows: an untyped rhinovirus designated as "Hank's (untyped)" and these additional rhinovirus types: type 4, type 6, type 8, type 10, type 13, type 17, type 19, type 21, type 29, type 39, type 56, type 58, type 59, type 60, type 64, type 68, type 74, type 75 and type 81.

In further tissue culture testing utilizing procedures similar to those described above, the compound 2-(3,4-dichlorophenoxy)-5-nitrobenzonitrile displayed inhibitory activity for the enteroviruses Coxsackie $B_2$ and Coxsackie $B_4$ but did not affect the multiplication (at the test concentrations of the subject compound utilized in testing) of the following viruses: influenza A, influenza WSN, influenza PR 8, parainfluenza 1, parainfluenza NDV (Newcastle's disease virus), adenovirus (untyped), Herpes simplex virus type 1 and a virus identified as feline calici virus, unconfirmed.

The results of the above-noted testing indicate that the compound 2-(3,4-dichlorophenoxy)-5-nitrobenzonitrile is particularly effective against Picornaviruses, i.e. small ribonucleic acid (rna) viruses, as for example, the Coxsackieviruses and Rhinoviruses. They further indicate that such compound has a broad spectrum of activity against Picornaviruses.

Utilizing the standard tissue culture testing and animal testing procedures described above, it was discovered that the subject compound 2-(3,4-dichlorophenoxy)-5-nitrobenzonitrile exhibited markedly greater antiviral activity than the comparison compound 5-(3,4-dichlorophenoxy)-2-nitrobenzonitrile. In the tissue culture testing, higher concentrations of 5-(3,4-dichlorophenoxy)-2-nitrobenzonitrile were required to produce a 50% reduction in cytopathic effect in testing against test viruses RV-1A, RV-2 and Cox $A_{21}$. In addition the comparison compound was not active against test viruses RV-5, RV-8 and RV-64 at the test concentrations employed. The comparison compound also failed to exhibit antiviral activity in the "Continuous Oral Feeding" test.

Another distinct advantage of the compound 2-(3,4-dichlorophenoxy)-5-nitrobenzonitrile is its low toxicity, in testing in rats it was found that the compound had an acute oral toxicity of about 5 grams/kilogram (kg) and with intraperitoneal administration greater than 2 grams/kg. Testing in beagle dogs indicated an acute oral toxicity of greater than 2 grams/kg.

Because of its many distinct advantages (broad spectrum antiviral activity at low compound concentration, low toxicity, antiviral activity when administered to animals orally, etc.), the compound 2-(3,4-dichlorophenoxy)-5-nitrobenzonitrile is the preferred embodiment of the present invention.

In using the compounds of the invention, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner effective to ensure continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an antiviral dosage of a compound of the invention to an animal. The compounds can be administered to animals parenterally (for example, by intraperitoneal, subcutaneous or intravenous injection) or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, such as, for example, the 0.156 $\mu$g/ml of 2-(3,4-dichlorophenoxy)-5-nitrobenzonitrile which caused a 50% reduction in cytopathic effect in testing against test virus RV-64.

Such compositions can contain from about 0.1 microgram or less of the active compound per milliliter of carrier to about 99 percent by weight of the active compound in combination with a pharmaceutically-acceptable carrier.

The compositions can be in solid forms such as tablets, capsules, granulations, feed mixes, feed supplements and concentrates, powders, granules or the like; as well as liquid forms such as sterile injectable suspensions, orally administered suspensions, or solutions. The pharmaceutically-acceptable carriers can include excipients surface active dispersing agents, suspending agents, tableting binders; lubricants, flavors and colorants. Suitable excipients are disclosed, for example, in texts such as Remington's Pharmaceutical Manufacturing, Thirteenth Edition, Mack Publishing Co., Easton, Pa. (1965).

Typical compositions will contain from about 0.1 $\mu$g of active compound per milliliter of carrier to about 0.0025 to about 0.05 to about 0.25 to about 0.5 to about one to about 10 to about 25 to about 50 percent by weight of active compound in a pharmaceutically-acceptable carrier.

In preferred compositions, the compound is employed in micronized form for solid compositions in admixture with a water dispersible pharmaceutically-acceptable carrier, such as a surface active dispersing agent, or in a liquid aqueous suspension or solution containing a pharmaceutically-acceptable suspending agent such as methylcellulose or hydroxypropyl methylcellulose or carboxymethylcellulose or a pharmaceutically-acceptable solvent such as ethanol.

Examples of representative aqueous suspensions, tablets and capsule formulations are described to further illustrate the invention but are not to be construed as a limitation thereon.

(A) Add to 50 ml of deionized water, the following components and mix in sequence: 1.0 g of Avicel RC591 (microcrystalline cellulose) 0.15 g of CMC 7HF (carboxymethylcellulose), 0.05 g of the surfactant Pluronic polyol F68 (polyoxypropylenepolyoxyethylene condensate), 0.1 g of the preservative potassium sorbate, 60.0 g of sucrose in 25 to 30 ml of deionized water, 2.0 g of 2-(3,4-dichlorophenoxy)-5-nitrobenzonitrile (preferably in micronized form) avoiding air entrapment if possible. Adjust the volume to 100 ml with deionized water and pass the final suspension through a suitable colloid mill or homogenizer. The resulting suspension is adapted for oral administration to administer, for example, 100 milligrams of the active compound per 5 milliliter dosage unit, or 200 mg per 10 ml dosage unit.

When necessary, any desired pharmaceutically-acceptable adjuvant used in suspension preparations by those skilled in the art, such as flavors, colors, preservatives and the like may be employed. The subject compounds can be used in suspensions, such as that described hereinabove, at concentrations from less than 1% to 10% weight/volume (w/v) or more.

(B) In a similar procedure, two grams of micronized 2-(3,4-dichlorophenoxy)-5-nitrobenzonitrile; 0.3 g SeaSpen PF (calcium carrageenan); 0.5 g CMC 7HF; 30 g sucrose; 0.1 g Pluronic polyol F68; 0.01 g sodium lauryl sulfate are mixed with sufficient deionized water to adjust final suspension volume to 100 ml.

(C) Similarly, two grams of micronized 2-(3,4-dichlorophenoxy)-5-nitrobenzonitrile; 2 g microcrystalline cellulose; 0.1 g Pluronic polyol F68; 0.01 g sodium lauryl sulfate; 0.1 g methylparaben (4-hydroxybenzoic acid methyl ester); 0.01 g propylparaben (4-hydroxybenzoic acid propyl ester) are mixed with sufficient deionized water to adjust final suspension volume to 100 ml.

(D) Mix in the following proportions: 7 g of micronized 2-(3,4-dichlorophenoxy)-5-nitrobenzonitrile with 228 g microcrystalline cellulose, 5.5 g corn starch and 7.5 g Methocel A15 (methyl cellulose). Form a wet granulation by adding deionized water. Screen the wet granulation and then dry. After screening the resulting dry granulation add 2.0 g magnesium stearate, blend and compress into 200 mg tablets.

(E) Mix in the following proportions: 5 g of micronized 2-(3,4-dichlorophenoxy)-5-nitrobenzonitrile with 230 g StaRx 1500 (modified food starch), 2.5 g magnesium stearate and 12.5 g corn starch and then compress the mixture into 250 mg tablets.

(F) Dissolve 5 grams of 2-(3,4-dichlorophenoxy)-5-nitrobenzonitrile in 100 ml polyethylene glycol 400 and pour into soft gelatin capsules, 250 mg per capsule.

(G) Mix in the following proportions: 5 g of micronized 2-(3,4-dichlorophenoxy)-5-nitrobenzonitrile with 210 g microcrystalline cellulose, 25 g lactose and 10 g corn strach. Fill into hard gelatin capsules, 250 mg of formulation per capsule.

Several of the tablet and capsule formulations described herein are based on a tablet or capsule dosage unit size of 250 milligrams. Other dosage unit sizes, as for example, a dosage unit of 50 mg or 100 mg are also contemplated and can be prepared essentially as described herein employing the various components at the appropriate concentration.

Conveniently, the composition is in the form of a dosage unit adapted for oral administration to a mammal, wherein said dosage unit contains an effective amount of said compound, said amount also being a non-toxic amount for said mammal. Conveniently, said composition is also in the form of a solid dosage unit comprising a water dispersible pharmaceutically-acceptable carrier and an effective amount of said compound.

Dosage units adaptable to oral administration such as tablets, capsules, lozenges, suspensions and the like can be formulations in which the preferred dosage of active subject compound per unit is about 1 milligram or less to about 5, to about 10, to about 25, to about 50, to about 100, to about 250, to about 300 milligrams or more per unit.

What is claimed is:

1. A compound of the formula

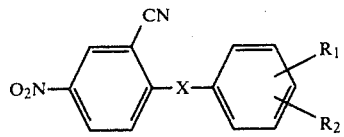

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro.

2. The compound of claim 1 wherein X represents O; $R_1$ represents bromo, chloro, fluoro, loweralkylsulfinyl or loweralkylsulfonyl and $R_2$ represents hydrogen, bromo, chloro or fluoro with the proviso that $R_2$ is hydrogen when $R_1$ is a substituent other than bromo, chloro or fluoro.

3. The compound of claim 2 wherein X represents O; $R_1$ represents bromo or chloro and $R_2$ represents hydrogen, bromo or chloro.

4. The compound of claim 1 which is 2-(3,4-dichlorophenoxy)-5-nitrobenzonitrile.

5. The compound of claim 1 which is 2-(2,4-dichlorophenoxy)-5-nitrobenzonitrile.

6. The compound of claim 1 which is 2-(4-bromophenoxy)-5-nitrobenzonitrile.

7. The compound of claim 1 which is 2-(4-chlorophenoxy)-5-nitrobenzonitrile.

8. The compound of claim 1 which is 2-(4-phenoxyphenoxy)-5-nitrobenzonitrile.

9. The compound of claim 1 which is 2-(4-(methylthio)phenoxy)-5-nitrobenzonitrile.

10. The compound of claim 1 which is 2-(4-(methylsulfinyl)phenoxy)-5-nitrobenzonitrile.

11. The compound of claim 1 which is 2-(4-methylsulfonyl)phenoxy)-5-nitrobenzonitrile.

12. The compound of claim 1 which is N,N-dimethyl-4-(2-cyano-4-nitrophenoxy)benzenesulfonamide.

13. The compound of claim 1 which is N,N-diethyl-4-(2-cyano-4-nitrophenoxy)benzenesulfonamide.

14. The compound of claim 1 which is 2-(4-benzoylphenoxy)-5-nitrobenzonitrile.

15. The compound of claim 1 which is 2-((4-chlorophenyl)thio)-5-nitrobenzonitrile.

16. A method for inhibiting viruses which comprises contacting viruses or virus host cells with an effective virus inhibiting amount of a compound corresponding to the formula

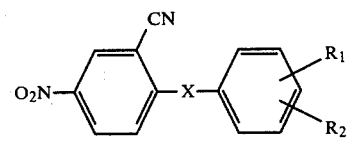

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro.

17. The method of claim 16 wherein the compound is contacted with a virus host cell.

18. The method of claim 16 wherein the compound is contacted with virus and mammalian cells.

19. The method of claim 16 wherein the viruses are picornaviruses.

20. The method of claim 16 wherein X represents O; $R_1$ represents bromo, chloro, fluoro, loweralkylsulfinyl or loweralkylsulfonyl and $R_2$ represents hydrogen, bromo, chloro or fluoro with the proviso that $R_2$ is hydrogen when $R_1$ is a substituent other than bromo, chloro or fluoro.

21. The method of claim 20 wherein X represents O; $R_1$ represents bromo or chloro and $R_2$ represents hydrogen, bromo or chloro.

22. The method of claim 21 wherein the compound is 2-(3,4-dichlorophenoxy)-5-nitrobenzonitrile.

23. The method of claim 21 wherein the compound is 2-(2,4-dichlorophenoxy)-5-nitrobenzonitrile.

24. The method of claim 21 wherein the compound is 2-(4-bromophenoxy)-5-nitrobenzonitrile.

25. The method of claim 21 wherein the compound is 2-(4-chlorophenoxy)-5-nitrobenzonitrile.

26. A method useful for inhibiting viruses which comprises administering to an animal an effective virus inhibiting amount of a compound corresponding to the formula

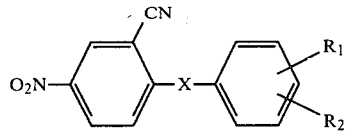

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro.

27. The method of claim 26 wherein the animal is a mammal.

28. The method of claim 26 wherein the animal is an animal infected with picornavirus.

29. The method of claim 28 wherein the picornavirus is a Rhinovirus.

30. The method of claim 28 wherein the picornavirus is a Coxsackievirus.

31. The method of claim 26 wherein X represents O; $R_1$ represents bromo, chloro, fluoro, loweralkylsulfinyl or loweralkylsulfonyl and $R_2$ represents hydrogen, bromo, chloro or fluoro with the proviso that $R_2$ is hydrogen when $R_1$ is a substituent other than bromo, chloro or fluoro.

32. The method of claim 31 wherein X represents O; $R_1$ represents bromo or chloro and $R_2$ represents hydrogen, bromo or chloro.

33. The method of claim 32 wherein the compound is 2-(3,4-dichlorophenoxy)-5-nitrobenzonitrile.

34. The method of claim 32 wherein the compound is 2-(2,4-dichlorophenoxy)-5-nitrobenzonitrile.

35. The method of claim 32 wherein the compound is 2-(4-bromophenoxy)-5-nitrobenzonitrile.

36. The method of claim 32 wherein the compound is 2-(4-chlorophenoxy)-5-nitrobenzonitrile.

37. A composition for inhibiting viruses comprising an inert carrier in combination with an effective virus inhibiting amount of a compound having the formula

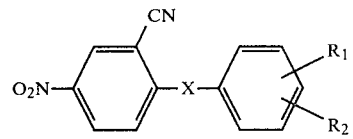

wherein X represents O or S; $R_1$ represents bromo, chloro, fluoro, phenoxy, loweralkylthio, loweralkylsulfinyl, loweralkylsulfonyl, loweralkylaminosulfonyl, diloweralkylaminosulfonyl or benzoyl; and $R_2$ represents hydrogen, bromo, chloro or fluoro with the proviso that $R_2$ is hydrogen when $R_1$ is a substituent other than bromo, chloro or fluoro.

38. The composition of claim 37 wherein the inert carrier is a non-toxic carrier.

39. The composition of claim 38 wherein the non-toxic carrier is a pharmaceutically-acceptable carrier.

40. The composition of claim 37 wherein X represents O; $R_1$ represents bromo, chloro, fluoro, loweralkylsulfinyl or loweralkylsulfonyl and $R_2$ represents hydrogen, bromo, chloro or fluoro with the proviso that $R_2$ is hydrogen when $R_1$ is a substituent other than bromo, chloro or fluoro.

41. The composition of claim 40 wherein X represents O; $R_1$ represents bromo or chloro and $R_2$ represents hydrogen, bromo or chloro.

42. The composition of claim 41 wherein the compound is 2-(3,4-dichlorophenoxy)-5-nitrobenzonitrile.

43. The composition of claim 41 wherein the compound is 2-(2,4-dichlorophenoxy)-5-nitrobenzonitrile.

44. The composition of claim 41 wherein the compound is 2-(4-bromophenoxy)-5-nitrobenzonitrile.

45. The composition of claim 41 wherein the compound is 2-(4-chlorophenoxy)-5-nitrobenzonitrile.

46. The composition of claim 40 wherein the composition is in the form of a dosage unit adapted for oral administration to a mammal and containing from 1 to about 300 milligrams of 2-(3,4-dichlorophenoxy)-5-nitrobenzonitrile per unit.

47. The composition of claim 46 wherein the composition is in the form of a solid dosage unit comprising a water dispersible pharmaceutically-acceptable carrier and an effective amount of said compound.

48. The composition of claim 46 wherein the composition is in the form of a tablet.

49. The composition of claim 46 wherein the composition is in the form of a capsule.

* * * * *